United States Patent [19]

Piso et al.

[11] Patent Number: 4,568,875
[45] Date of Patent: Feb. 4, 1986

[54] MOISTURE CORRECTED DENIER MEASUREMENT

[75] Inventors: John S. Piso, Framingham; David M. Geary, Natick, both of Mass.

[73] Assignee: Micro Sensors Incorporated, Holliston, Mass.

[21] Appl. No.: 568,671

[22] Filed: Jan. 6, 1984

[51] Int. Cl.⁴ ............................................ G01R 27/26
[52] U.S. Cl. .................................... 324/61 R; 73/160; 73/159
[58] Field of Search .............. 57/265, 264, 81; 73/73, 73/74, 159, 160; 324/61 R

[56] References Cited

U.S. PATENT DOCUMENTS

| | | | |
|---|---|---|---|
| 3,873,927 | 3/1975 | Overall | 324/61 R |
| 3,879,660 | 4/1975 | Piso | 324/61 R |
| 3,882,381 | 5/1975 | Gregory | 324/61 R |
| 3,990,005 | 11/1976 | Abbe | 324/61 R |
| 4,208,625 | 6/1980 | Piso | 324/61 R |

FOREIGN PATENT DOCUMENTS 320765  2/1972  U.S.S.R. ................................. 73/74

OTHER PUBLICATIONS

Dobkin: "1.2 Volt Reference", National Semi.-App. Note, #AN56, published Dec. 1971.

Primary Examiner—Stanley T. Krawczewicz
Assistant Examiner—Jose M. Solis
Attorney, Agent, or Firm—Parmelee, Boltinger & Bramblett

[57] ABSTRACT

Measurements of yarn denier using capacitance transducers are automatically corrected for moisture. Samples of the yarn to be run are tested at different moisture levels at different frequencies in each of two capacitance transducers. The difference in the apparent denier outputs of the two transducers has been found to be proportional to moisture content. The difference is added to one of the measured values to provide a more correct reading. The difference may be further corrected by a factor derived from the slopes of the curves of transducer output vs. moisture and the slope of the curve of skein denier vs. moisture.

11 Claims, 2 Drawing Figures

MOISTURE CORRECTED DENIER MEASUREMENT

BACKGROUND OF THE INVENTION

U.S. Pat. No. 3,879,660 which issued Apr. 22, 1975 to John S. Piso discloses a system for continuously measuring changes in materials and, specifically, for monitoring denier of synthetic yarns. The yarn passes through the plates of a pair of capacitors connected in a capacitance bridge. The bridge unbalance output is differentially amplified and fed to a synchronously operated phase sensitive detector. The direct current output of the detector is utilized as an indicator of denier.

The apparatus disclosed in the referenced patent has proved to be a commercially successful device. However, synthetic yarns tend to pick up moisture from the atmosphere and the presence of such moisture in the capacitor dielectric may alter the bridge balance, thereby resulting in a false denier measurement. The prior art has disclosed or suggested the use of capacitance transducers at plural frequencies for the measurement of moisture and other variables. However, these prior art disclosures involve a relatively complex mathematical treatment of the output signals and, in most instances, utilize the output ratio to derive desired information. Examples of such disclosures will be found in U.S. Pat. Nos. 3,155,898 of H. R. Chope; 3,155,900 and 3,155,901 of A. F. G. Hanken; 3,155,902 of G. W. Walls; 3,241,062 of C. W. Baird; and 3,290,588 of A. Norwich. Accordingly, it is a primary object of the present invention to provide simpler method and apparatus for employing plural frequency capacitance transducer measurements of yarn denier corrected for moisture. Other objects are: to provide such method and apparatus which does not require ratioing or complex mathematical treatment of signal outputs; which may be precalibrated for each type of yarn; and which yields accurate measurements of yarn denier and denier variability regardless of the moisture contained in the yarn. The manner in which these objects are achieved will be more apparent from the following description and appended claims.

SUMMARY OF THE INVENTION

The invention comprises method and apparatus for accurately measuring the denier of a moisture containing yarn. A first denier measurement of a length of yarn is obtained by means of a first capacitor transducer operating at a first frequency. A second denier measurement of the same yarn is obtained by means of a second capacitor transducer operating at a second frequency which is lower than the first frequency. The difference between the first and second denier measurement is proportional to contained moisture and is added to the first denier measurement to obtain a moisture-corrected measurement.

DESCRIPTION OF THE PREFERRED EMBODIMENT

Figure 1:
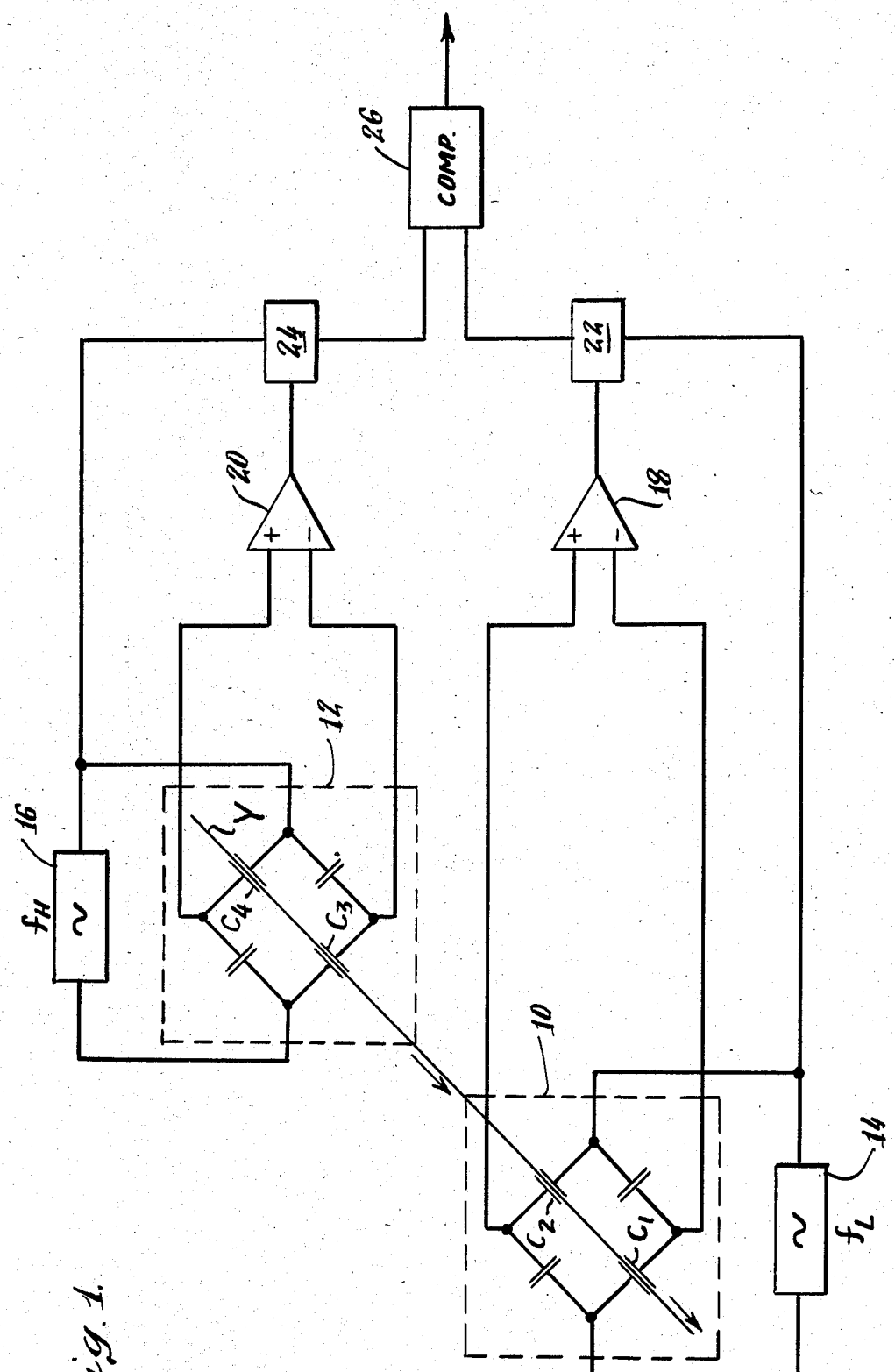
FIG. 1 is a simplified schematic diagram of a circuit for accomplishing the objects of the invention.

FIG. 1 illustrates a specific embodiment of this invention incorporating two capacitance bridge transducers 10, 12 of the type disclosed in the referenced Piso patent, operating from separate signal generators 14, 16 at 25 kHz and 12 MHz, respectively. Alternatively, the lower freguency might be from 1-100 kHz and the higher frequency from 1-50 MHz. In an actual embodiment, the low frequency transducer 10 was a model M/7008 transducer and the high frequency transducer 12 was a model M/1002 transducer, both manufactured by Micro Sensors Inc. of Holliston, Mass.

As explained in the Piso patent, a yarn Y under test is passed through the plates of opposed capacitors $C_1$, $C_2$ and $C_3$, $C_4$ in each bridge. The output of each bridge is applied to the input of a respective differential amplifier 18, 20 and the amplified signal is then processed by further circuitry 22, 24 including demodulators, filters, amplifiers, etc. to yield outputs representative of denier measurements. These outputs in turn are acted upon by a moisture compensation circuit 26 which functions as described below to yield outputs of moisture-corrected denier and of yarn moisture content. To accomplish these results, the circuit 26 is supplied or programmed with information obtained from test samples of the yarn to be processed, as will hereinafter be explained. Thereafter, the system will accurately measure yarn denier immediately after a spinning package has doffed, regardless of the moisture contained in the yarn.

It has been discovered that the curves of apparent denier versus relative humidity (of a yarn exposed for a sufficient time to accumulate moisture content) are essentially linear. It has also been discovered that the slopes of the linear curves are different, the slope of the low frequency curve being greater than that of the high frequency curve. However, it has also been discovered that, for any given moisture level, the high frequency denier measurement less the low frequency denier measurement is a number which is proportional to moisture. Adding this to the high frequency denier measurement results in a close approximation to the actual skein denier.

An even closer approximation may be achieved by multiplying the moisture proportional number by a correction factor derived from the slopes of the high and low frequency curves and the empirically determined slope of the skein curve. This will be more apparent from the following specific example, taken together with the curves illustrated in FIG. 2.

EXAMPLE

Several packages of Monsanto nylon yarn BB-LK122782 were allowed to reach moisture equilibrium at each of several different relative humidity levels by holding it at such level for eighteen hours. A standard denier reel and electronic balance were then employed to obtain the skein denier at each moisture level. The results were averaged and plotted as "skein" denier 28 in FIG. 2 and found to be linear. (The term "regain moisture" in FIG. 2 refers to the moisture which would be regained by oven dried yarn at each relative humidity value as a percentage of the yarn weight.)

After obtaining skein denier by direct measurement, a number of similarly treated samples of the same type yarn were run through the capacitance bridges 10, 12 operating at 25 kHz and 12 MHz, respectively. The indicated denier measurements from each bridge transducer were then averaged and the results plotted on the same graph as the skein denier. The graph 30 of the low frequency denier measurement $D_L$ and the graph 32 of the high frequency denier measurement $D_H$ were similarly found to be linear.

The data for the three curves were subjected to linear regression operations and their formulae determined to be as follows:

$$D_{Skein} = \%RH \times 0.0306 + 128.2728$$

$$D_H = \%RH \times 0.5918 + 93.4784$$

$$D_L = \%RH \times 1.2299 + 53.9162$$

in the usual linear equation form $y = mx + b$ where the x terms are relative humidity. For a given type of yarn, the slopes m were found to remain relatively constant. The b constants varied slightly from package to package due to small variations in average denier. In the application of this invention, it is the slopes that are of primary interest.

It has been discovered that the difference between the indicated denier at the high and low frequencies is proportional to the moisture (M) contained in the yarn.

$$M = K\Delta D = K(D_H - D_L)$$

By testing sufficient samples of each type of yarn and subjecting the data to a linear regression, we can obtain a linear equation for such yarn $$M = m(\Delta D) + b.$$

By inserting this equation into the compensation circuit 26, actual moisture readouts for the same type yarn may be subsequently obtained.

It has also been discovered that the apparent deniers derived from the high and low frequency transducers are so related that they may be readily converted to yield an output denier ($D_o$) very closely related to the skein denier. The relationship is $$D_o = D_H + \left[ (D_H - D_L) \frac{m_S - m_H}{m_H - m_L} \right]$$

where $m_S$, $m_H$, $m_L$ are the slopes of the skein, high frequency, and low frequency denier measurements, respectively.

Figure 2:
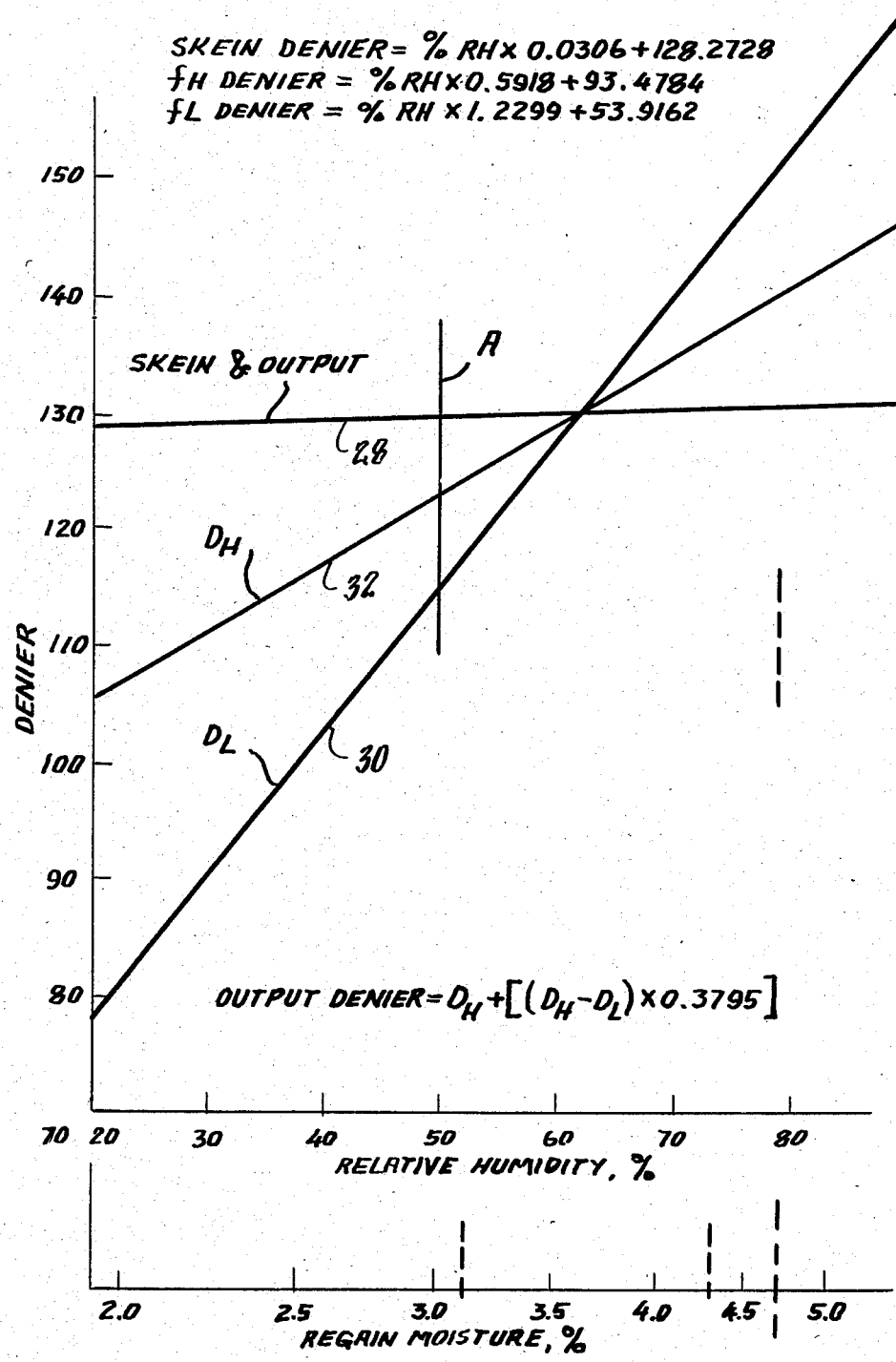
FIG. 2 is a graph of denier versus humidity or moisture for a specific nylon yarn including curves for a low frequency transducer, a high frequency transducer, and a corrected output corresponding to skein denier.

Applying the preceding equation to the specific example previously described and charted in FIG. 2, the "correction factor" formed by the slope relationship becomes $$\frac{m_S - m_H}{m_H - m_L} = \frac{.0306 - .5918}{.5918 - 1.2299} = 0.8795$$

This factor is also supplied to the compensation circuit which thereafter calculates the corrected denier $D_o$ from $D_H$ and $D_L$. As an example, along the line A of FIG. 2, $D_H = 123.0$ and $D_L = 115.5$, then $$D_o = 123 + [(123 - 115.5) 0.8795]$$
$$= 123 + 6.6$$
$$= 129.6$$

which also corresponds to the previously determined skein denier. Accordingly, it will be apparent that by means of the present invention, it has become possible to obtain both a moisture reading and a moisture-corrected denier reading from a pair of apparent denier outputs of capacitance transducers operating at different frequencies. Further, the mathematics involved is extremely simple and easily applied.

It is believed that the many advantages of this invention will now be apparent to those skilled in the art. It will also be apparent that many modifications and variations may be made therein without departing from its spirit and scope. Accordingly, the foregoing description is to be construed as illustrative only, rather than limiting. This invention is limited only by the scope of the following claims.

What is claimed is:

1. Apparatus for accurately measuring the denier of moisture-containing yarn which comprises:

first capacitor transducer means operating at a first frequency for obtaining a first denier measurement of a length of yarn;

second capacitor transducer means operating at a second frequency lower than said first frequency for obtaining a second denier measurement of said length of yarn; and means for obtaining a moisture-corrected measurement by adding to said first denier measurement a correction proportional to moisture comprising the difference between said first denier measurement and said second denier measurement.

2. The apparatus of claim 1 wherein each of said transducer means comprises a capacitance bridge.

3. The apparatus of claim 1 or 2 wherein said first frequency is within the range of 1-50 MHz and said second frequency is within the range of 1-100 kHz.

4. A method of accurately measuring the denier of moisture-containing yarn which comprises:

obtaining a first denier measurement of a length of yarn by means of a first capacitor transducer operating at a first frequency;

obtaining a second denier measurement of said length of yarn by means of a second capacitor transducer operating at a second frequency lower than said first frequency; and obtaining a moisture-corrected measurement by adding to said first denier measurement a correction proportional to moisture comprising the difference between said first denier measurement and said second denier measurement.

5. The method of claim 4 wherein each of said first and second transducers is a capacitance bridge.

6. The method of claims 4 or 5 wherein said first frequency is within the range of 1-50 MHz and said second frequency is within the range of 1-100 kHz.

7. A method of accurately measuring the denier of moisture-containing yarn which comprises:

establishing a first linear relationship for the variation of skein denier with humidity for a test sample of yarn;

establishing a second linear relationship for the variation of denier of said yarn with humidity by means of a first capacitance transducer operating at a first frequency;

establishing a third linear relationship for the variation of denier of said yarn with humidity by means of a second capacitance transducer operating at a second frequency lower than said first frequency;

obtaining a first apparent denier measurement of a length of yarn by means of said first capacitor transducer operating at said first frequency;

obtaining a second apparent denier measurement of said length of yarn by means of said second capacitor transducer operating at said second frequency; and obtaining a corrected measurement by adding to said first apparent denier measurement a correction approximately proportional to moisture comprising said first denier measurement less said second denier measurement.

8. The method of claim 7 wherein each of said first and second transducers is a capacitance bridge.

9. The method of claim 7 or 8 wherein said first frequency is within the range of 1–50 MHz and said second frequency is within the range of 1–100 kHz.

10. The method of claim 7 wherein said moisture proportional correction is multiplied by a correction factor.

11. The method of claim 10 wherein said correction factor comprises
   (A) the slope of said first linear relationship less the slope of said second linear relationship divided by
   (B) the slope of said second linear relationship less the slope of said third linear relationship.

* * * * *